(12) United States Patent
Madson (10) Patent No.: US 9,625,468 B1
(45) Date of Patent: Apr. 18, 2017

(54) METHOD OF ISOLATING AND ANALYZING OLIGOSACCHARIDES IN GLYCOPROTEINS

(71) Applicant: Michael A. Madson, Ames, IA (US)

(72) Inventor: Michael A. Madson, Ames, IA (US)

(*) Notice: Subject to any disclaimer, the term of this patent is extended or adjusted under 35 U.S.C. 154(b) by 0 days.

(21) Appl. No.: 14/945,915

(22) Filed: Nov. 19, 2015

(51) Int. Cl.
*G01N 33/68* (2006.01)
*C12P 19/12* (2006.01)
*G01N 30/96* (2006.01)

(52) U.S. Cl.
CPC .......... *G01N 33/6812* (2013.01); *C12P 19/12* (2013.01); *G01N 30/96* (2013.01); *Y10T 436/143333* (2015.01); *Y10T 436/25* (2015.01)

(58) Field of Classification Search
CPC ............... G01N 33/68; G01N 33/6803; G01N 33/6812; Y10T 436/143333; Y10T 436/25; Y10T 436/25125; Y10T 436/25375; Y10T 436/255
USPC ....... 436/86, 87, 89, 94, 161, 174, 175, 177, 436/178
See application file for complete search history.

(56) References Cited

U.S. PATENT DOCUMENTS

2004/0039192 A1* 2/2004 Packer .................... C07H 1/08 536/123
2004/0096933 A1* 5/2004 Huang ..................... C07H 1/08 435/68.1
2007/0105179 A1 5/2007 Madson
2011/0275108 A1* 11/2011 Nishimura ............ C07C 271/02 435/29

FOREIGN PATENT DOCUMENTS

WO 90/04596 * 5/1990

OTHER PUBLICATIONS

Madson et al (abstract). Abstracts of Papers, 247th ACS National Meeting & Exposition, Dallas, TX, United States, Mar. 16-20, 2014.*
Patel et al. Biochemistry, vol. 32, 1993, pp. 679-693.*
Karlsson et al. Analytical Biochemistry, vol. 305, 2002, pp. 173-185.*

* cited by examiner

Primary Examiner — Maureen Wallenhorst
(74) *Attorney, Agent, or Firm* — Zarley Law Firm, P.L.C.

(57) ABSTRACT

A method for isolating derivatives of general O-linked amino acids including derivatives of O-tyrosine linked kappa casein di-O-sulfo tetrasaccharide and of O-di-phospho serine linked bovine submaxillary mucin disaccharide is provided. These derivatives are isolated and analyzed by further enzymatically separating the N-linked oligosaccharides from the O-linked oligosaccharides and then cleave O-linked oligosaccharides by decreasing the pH levels such that de-amidations are allowed. This de-amidation results in individual O-linked glycan amino acid components removed from the original glycoprotein. The O-linked glycan amino acid components are thus isolated from the glycoprotein, and can be individually analyzed.

15 Claims, 8 Drawing Sheets

METHOD OF ISOLATING AND ANALYZING OLIGOSACCHARIDES IN GLYCOPROTEINS

BACKGROUND OF THE INVENTION

This invention relates to methods of isolating and analyzing oligosaccharides from glycoproteins. More specifically, this invention relates to laboratory methods that can be used in order to isolate derivatives of O-tyrosine linked kappa casein di-O-sulfo tetrasaccharide and of O-di-phospho serine linked bovine submaxillary mucin disaccharide and O-linked glycan amino acids generally. O-linked oligosaccharides are oligosaccharides that are covalently attached to serine, threonine, or very rarely tyrosine residues on a glycoprotein.

Cancer is a disease that has a major impact on societies across the globe. According to the *National Cancer Institute* (2015), an estimated 1,658,370 new cases of cancer will be diagnosed and 589,430 people will die from the disease this year in the United States alone. As a result, researchers and their institutions are in a continuous search for substances that are effective in promoting anti-cancer biological activity—whether the substances prevent the onset of cancer or, alternatively, slow down or stop the growth of cancer.

Recent scientific developments by Guo et al., *Curr. Opin. Chem Biol.* (2009) 13 5-6, and by Lindhorst, *Bielstein J. Org. Chem.* (2012) 8 804-818, have shown the utility of O-linked glycan amino acids such as those linked to serine, threonine, and very rarely tyrosine as potential cancer vaccines and synthetic glycopeptides for use in general immunostimulants. Thus, a principal objective of the present invention is to provide a method for isolating O-linked oligosaccharides in order to determine the oligosaccharide anti-cancer potential.

Despite advances in the art, problems still remain. Many obstacles arise when isolating the oligosaccharides from glycoproteins that in turn limit the understanding of oligosaccharide anti-cancer activity. In particular, problems exist with isolating O-linked glycan amino acids with specificity. Current methods require the use of reductive methods that are both costly and stifle the depth of research because these methods and systems are not as sensitive or stable. For instance, in U.S. Patent Publication 2007/0105179 A1 discloses separating and detecting N- and O-linked oligosaccharides in glycoproteins via non-degradative enzymatic cleavage. This method does not provide for the identification and isolation of particular O-linked glycan amino acids—such as derivatives of O-tyrosine linked kappa casein di-O-sulfo tetrasaccharide and of O-di-phospho serine linked bovine submaxillary mucin disaccharide and for general O-linked glycan amino acids—in glycoproteins that are isolated using the method disclosed herein. Therefore, a need in the art exists to address these deficiencies.

Thus, a primary object of the invention is to provide a method and system that improves upon the state of the art.

Another object of the invention is to provide a method that is simple and maximizes a preferred pH stability required to specifically isolate an O-linked glycan amino acid.

These and other objects, features, or advantages of the present invention will become apparent from the specification, drawings, and claims.

SUMMARY OF THE INVENTION

A method of isolating derivatives of O-tyrosine linked kappa casein di-O-sulfo tetrasaccharide and of O-di-phospho serine linked serine linked bovine submaxillary mucin disaccharide and for O-linked glycan amino acids in general. The method includes the step of treating a glycoprotein sample by known methods in order to cleave and separate N- and O-linked oligosaccharides. Further, the treated glycoprotein is removed from the cation exchange resin in the ammonium form by adding a predetermined amount of ammonium hydroxide solution. The method also includes the steps of adding the removed sample to a tube with a predetermined amount of water. Also included in the method is adding a predetermined amount of sodium borohydride to make the corresponding alditol and removing any remaining asparagine linked oligosaccharides. The method includes the step of allowing the solution to stand at ambient temperature and capped for a predetermined amount of time. For example, a capped time period of 4 hours would be at ratio with 18 hours of uncapped time period. Additionally, the method involves evaporating the contents of the tube to an approximate volume. In one embodiment, the volume is 0.2 mL. The method then includes the steps of adding a volume of water to the remainder of the solution and passing the solution through a sodium form cation exchange resin with washing an additional amount of water before freezing the resulting solution. Lastly, the method includes preparing and analyzing the solution to determine the isolation success during the method.

In an alternative embodiment of the invention, the method includes the step of treating a glycoprotein sample by known methods in order to cleave and separate N- and O-linked oligosaccharides. Further, the treated glycoprotein is removed from the cation exchange resin in the ammonium form by adding a predetermined amount of ammonium hydroxide solution. The method also includes the steps of then adding the treated sample to a tube with a predetermined amount of water. Also included in the method is adding a predetermined amount of sodium borohydride to make the corresponding alditol. The method then includes eluting the first solution from the ammonium cartridge used to treat the sample by adding a predetermined amount of ammonium hydroxide solution. The method includes the step of allowing the solution to stand at ambient temperature and capped for a predetermined amount of time. For example, a capped time period of 4 hours would be at ratio with 18 hours of uncapped time period. The solution is then evaporated for an approximate amount of time. In one embodiment, this volume is 0.2 mL. The method includes adding a predetermined amount of sodium borohydride solution. In one embodiment, the sodium borohydride solution volume is 3 μL and concentration 4N.

The method includes the steps of injecting the treated sample on to a column read by an analysis device. Also, the method includes the step of collecting the solution containing the compound located at the chromatographic first peak by placing the analysis device tubing into a separate vial. Further, the method includes the step of collecting the solution containing the compound located at the chromatographic second peak by placing the analysis device tubing into another separate vial. The method includes the steps of pushing the contents of each vial through a separate ammonium form cation exchange cartridge and collecting in a tube of predetermined volume, evaporating the contents to a predetermined volume, adding a predetermined amount of water and pushing the solution through a sodium ion cation exchange resin. Lastly, the method includes the steps of freezing or analyzing the resultant solution.

DETAILED DESCRIPTION

Figure 1:
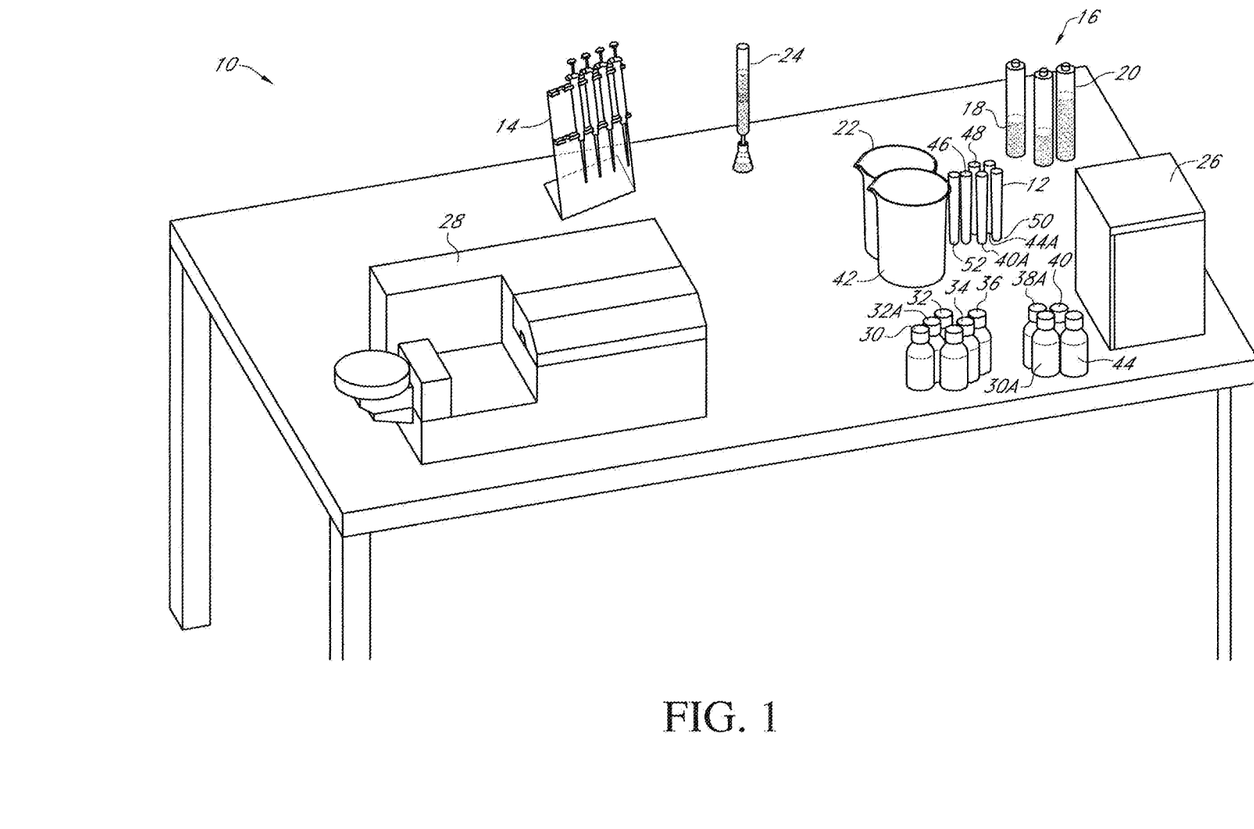
FIG. 1 depicts a perspective view of a system to isolate an O-linked oligosaccharide.

Referring to the figures, FIG. 1 depicts a system 10 utilized in order to isolate and analyze derivatives of O-tyrosine linked kappa casein di-O-sulfo tetrasaccharide and of O-di-phospho serine linked bovine submaxillary mucin disaccharide and for O-linked glycan amino acids generally. The system includes a test tube 12, a plurality of pipets 14, ion exchange cartridges 16 including one in the ammonium form 18 and one in the sodium form 20, a plurality of beakers 22, an elution column 24, and a freezer 26. In addition, the system 10 in FIG. 1 can include one or more analysis devices 28 such as a mass spectrometer (MS), or a high performance anion exchange chromatograph with pulse amperometric detection (HPAEC-PAD).

Figure 2:
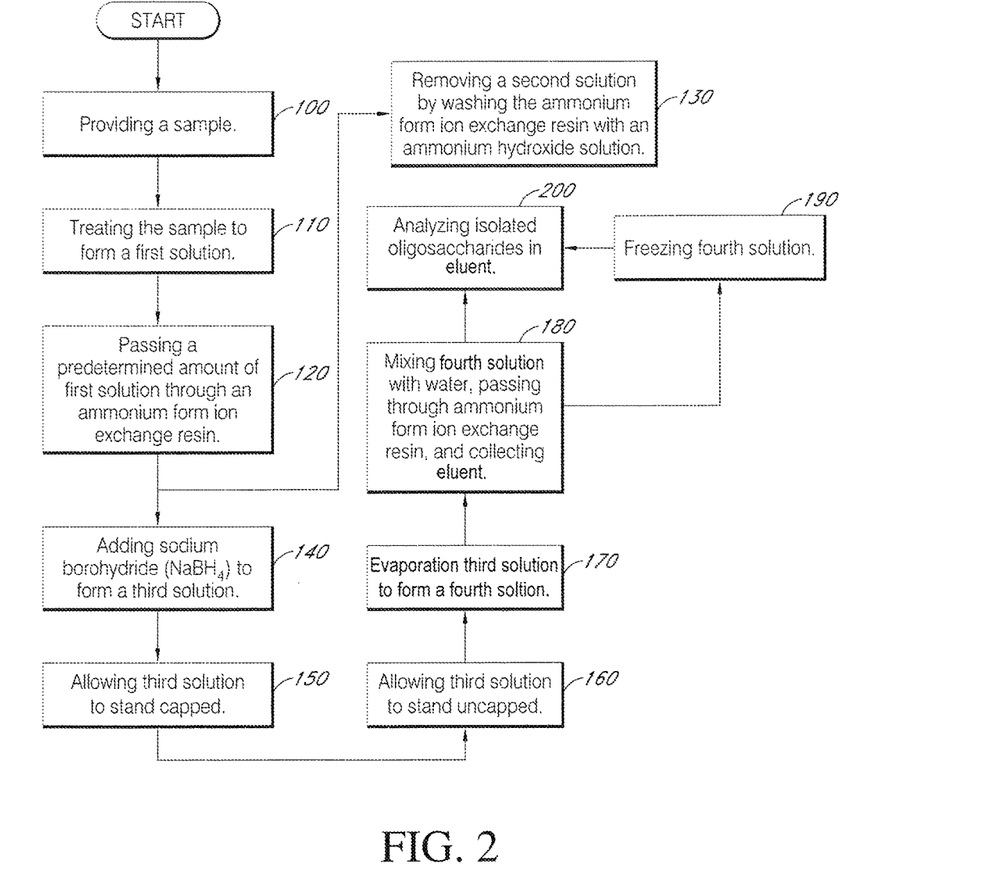
FIG. 2 depicts a flow diagram of a method of isolating O-linked glycan amino acids from a glycoprotein.
Figure 3:
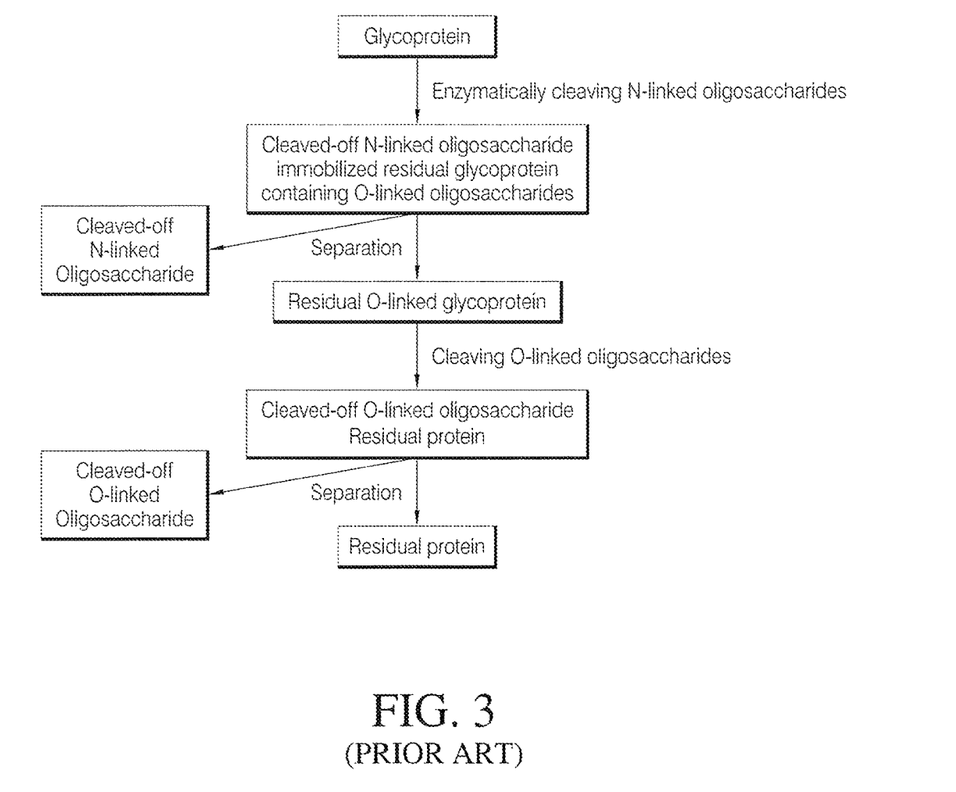
FIG. 3 depicts a flow diagram of a method of removing N-linked and O-linked oligosaccharides from a glycoprotein.

The method as shown in FIG. 2, using the system of FIG. 1, begins as step 100 by providing a sample 30. In one embodiment, the sample 30 is a glycoprotein bovine submaxillary mucin. In another embodiment, the sample 30 is kappa casein. In one exemplary embodiment the sample 30 has a mass of 0.3 mg and is mixed with 1.0 mL of water in a 1.5 mL test tube 12. At step 110, the sample 30 is treated by known methods, such as those disclosed by Madson in U.S. Patent Publication 2007/0105179 A1. As depicted in FIG. 3, the sample 30 is treated to enzymatically separate N- and O-linked oligosaccharides to form a first solution 32. In an exemplary arrangement, the sample is treated with PNGase F 34 and then sodium borohydride 36 ($NaBH_4$).

At step 120, a predetermined amount of the first solution 32 is passed through the ammonium form cation exchange resin 18. A second solution 38 is removed from the resin by adding a predetermined amount of ammonium hydroxide solution at step 130. In one embodiment, the ammonium hydroxide solution is 2N $NH_4OH$. Additionally, in a preferred embodiment the amount of ammonium hydroxide solution added is 1.0 mL. Next, at step 140, a predetermined amount of sodium borohydride 36 is pipetted into the second solution 38 to form the third solution 40. In one arrangement, 3.0 µL solution of sodium borohydride 36 is added, which in one embodiment is 4N solution of sodium borohydride 36.

The third solution 40 is allowed to stand at ambient temperature, capped, for a predetermined amount of time at step 150. In one embodiment, the time period is four hours. At step 160, the third solution 40 is then uncapped and allowed to stand at ambient temperature for a predetermined amount of time. For instance, if capped time is four hours, the uncapped time is eighteen hours.

After the predetermined amount of time has elapsed, the third solution 40 is evaporated at step 170. In one embodiment, the third solution 40 is evaporated until approximately 0.2 mL of the third solution 40 is left. Next at step 180, the remainder of the third solution 40 is mixed with water 42 and passed through the sodium form cation exchange resin 20 and collecting a fourth solution or resulting solution 44 off of the ion exchange cartridge 13. In one embodiment, approximately 1.0 mL water 42 is added.

Figure 6:
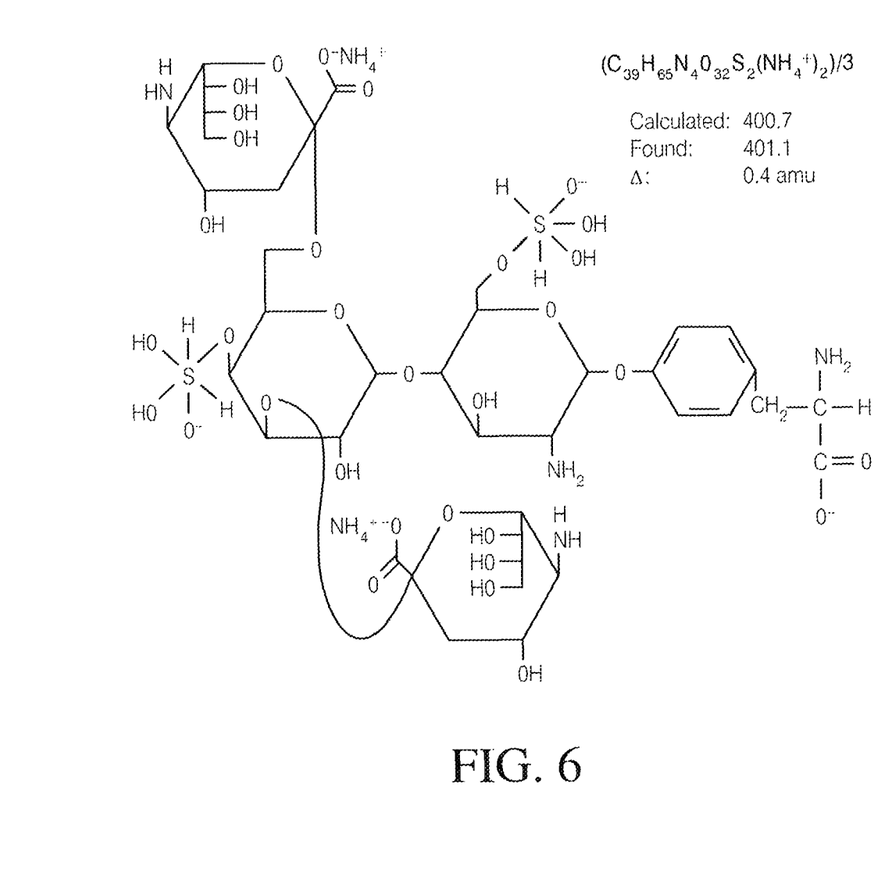
FIG. 6 depicts a structure consistent with O-tyrosine linked kappa casein di-O-sulfo tetrasaccharide.

At step 190, the fourth solution 44 is placed in a freezer 26 until thawed for further analysis at step 200. Thawing can be accomplished by placing the resulting fourth solution 44 in one of the beakers 22 filled with water 42. In one embodiment, the fourth solution 44 is analyzed by infusion into an API Triple Quadrapole MS. In another embodiment, the fourth solution 44 is analyzed by HPAEC-PAD using an MA1 column with 310 mM NaOH and a flow rate of 0.2 mL per mintue with a borate column inserted before the analytical MA1 column. As shown in FIG. 6, the structure consistent with O-tyrosine linked kappa casein di-O-sulfo tetrasaccharide is identified.

Figure 4:
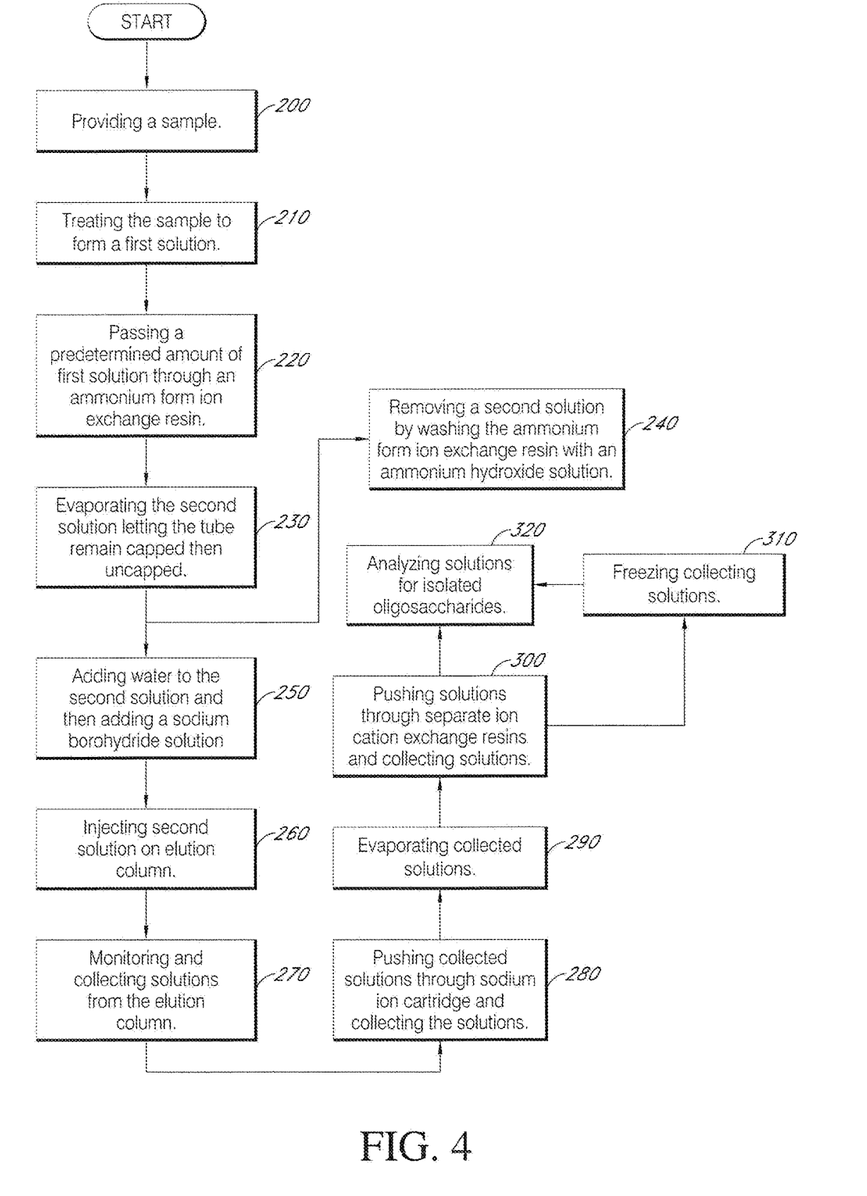
FIG. 4 is a flow diagram of a method of isolating O-linked glycan amino acids from a glycoprotein.
Figure 5:
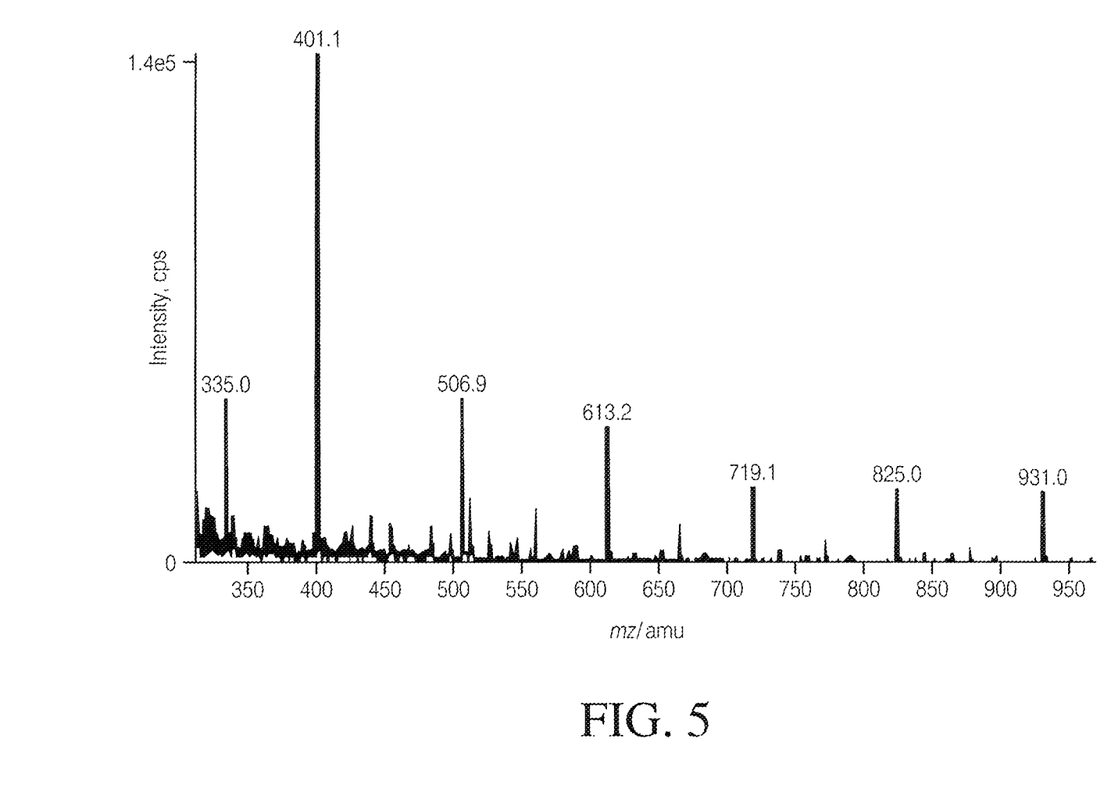
FIG. 5 depicts mass spectrum from the larger of two peaks resulting from HPAEC-PAD.

In an alternative embodiment, the above method can be instituted with slight variation. The method as shown in FIG. 4, using the system of FIG. 1, begins at step 200 by providing the sample 30A. In one embodiment, the sample 30A is a glycoprotein bovine submaxillary mucin. In another embodiment, the sample 30A is kappa casein. At step 210, the sample 30A is treated by known methods, such as those depicted in FIG. 3. In an exemplary arrangement, the sample is treated with PNGase F 34 and then sodium borohydride 36. At step 220, the remaining first solution 32A is passed through the ammonium form cation exchange resin 18. At step 230, a predetermined amount of the first solution 32A is evaporated. In one embodiment, the first solution 32A is evaporated to 0.2 mL remaining. Additionally at step 230, the tube 12 is then capped for a predetermined amount of time and then uncapped for a predetermined amount of time. In one embodiment, the tube 12 is left capped for 4 hours and left uncapped for 18 hours. A second solution 38A is removed from the resin by adding a predetermined amount of ammonium hydroxide solution at step 240. In one embodiment, the ammonium hydroxide solution is 2N $NH_4OH$. Additionally, in a preferred embodiment, the amount of ammonium hydroxide solution added is 1.0 mL.

At step 250, a predetermined amount of sodium borohydride 36 is added, and in one arrangement water is also added to form a third solution. In one arrangement, the amount of sodium borohydride 36 added is 3 microliters, which in one embodiment is 4N solution of sodium borohydride 36. The third solution 38A is injected onto an elution column 24 at step 260, which in one arrangement is a Thermo Fisher MA1 elution column. In one preferred embodiment, the third solution injected onto the column is approximately 0.01 mL. A fourth solution 40A, located at the first chromatographic peak, is monitored and collection from the elution column 24 and deposited in one of the test tubes 12. The fourth solution 40A and a fifth solution 44A collected from the solution column 24 at the second chromatographic peak are pushed through separate ammonium form a cation exchange cartridges 18 to form a sixth solution 124 resulting from the fourth solution 40A and a seventh solution 48 resulting from the fifth solution 44, collected in separated tubes 12 at step 280.

Figure 7:
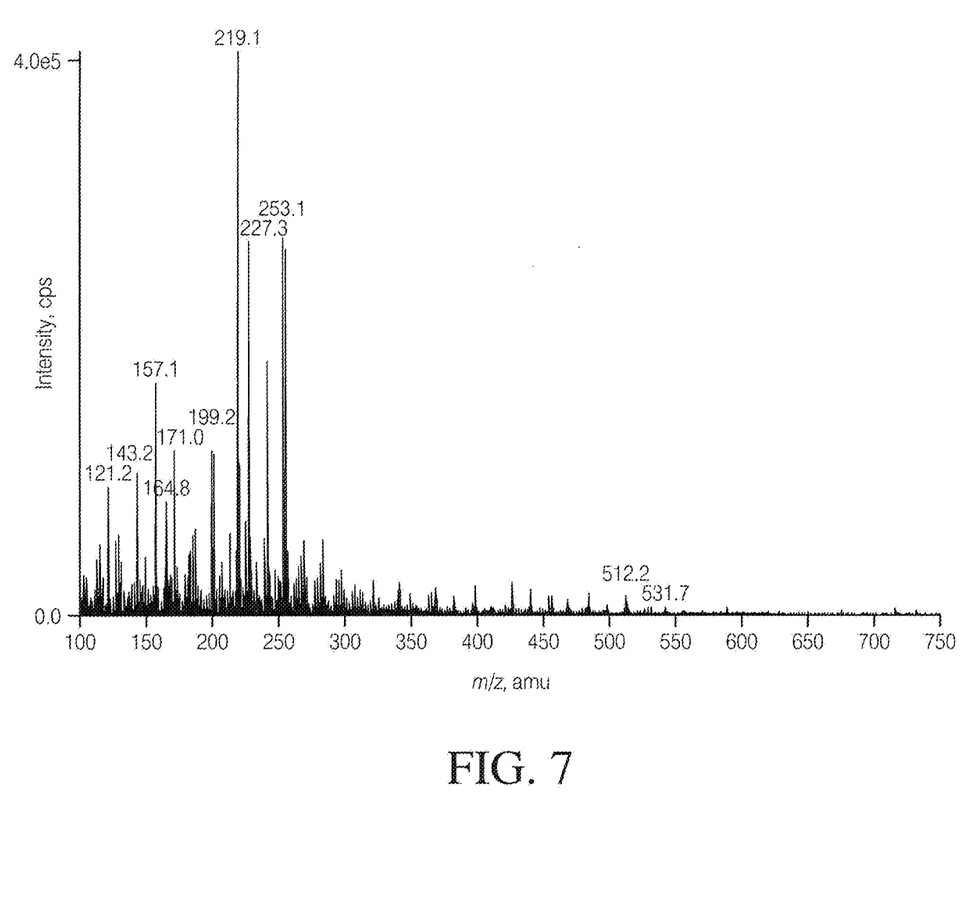
FIG. 7 depicts a mass spectrum obtained using a method of isolating O-linked glycan amino acids from a glycoprotein.

The sixth solution 46 and the seventh solution 48 are evaporated at step 290. In one embodiment, the sixth solution 46 and the seventh solution 48 solution are evaporated to approximately 0.2 mL and 1.0 mL of water is subsequently added. At step 300, the sixth solution 46 and the seventh solution 48 are pushed through separate sodium ion cation exchange resins 20 to form an eighth solution 50 and a ninth solution 52. The eighth solution 50 and the ninth solution 52 are placed in a freezer 26 at step 310 until thawed for further analysis at step 320. In one embodiment, analysis is completed by the analysis device 28, such as in one embodiment, an API MS by infusion onto a Triple Quadrapole MS is used. In other embodiments, analysis is completed by MALDI-TOF MS or by HPAEC-PAD. As shown in FIG. 7, the structure consistent with O-di-phospho serine linked bovine submaxillary mucin disaccharide is identified.

Previous methods provide for separating cleaved-off N-linked oligosaccharides from cleaved-off O-linked oligosaccharides, such that the cleaved-off N-linked and O-linked oligosaccharides can be separately detected as shown in FIG. 3. Typically, these systems require degradative steps during cleavage without specifically isolating an O-linked glycan amino acid such as O-tyrosine linked kappa casein di-O-sulfo tetrasaccharide or O-di-phospho serine linked bovine submaxillary mucin disaccharide.

Figure 8:
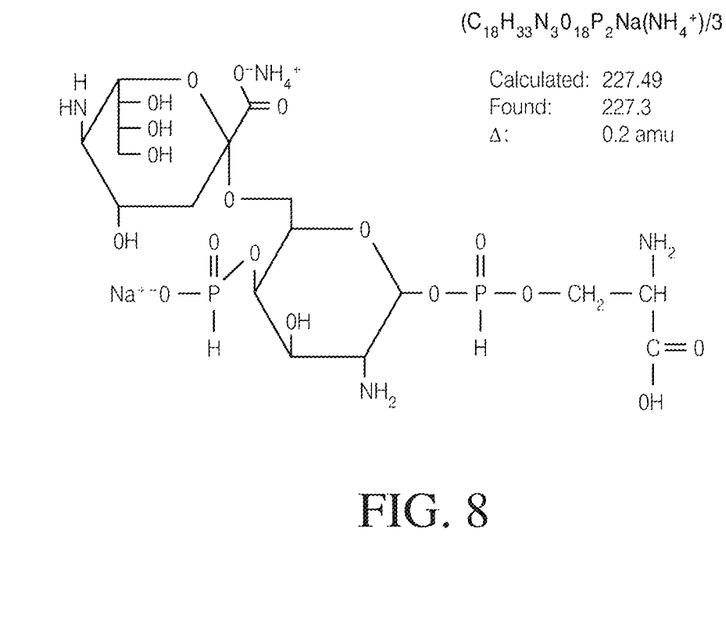
FIG. 8 depicts a structure consistent with O-di-phospho serine linked serine linked bovine submaxillary mucin.

By contrast, the methods disclosed herein provide for isolating and analyzing O-linked oligosaccharides at a predetermined pH in order to maximize de-amidation, leaving only the derived amino acid linked glycan for analysis as depicted by FIGS. 6 and 8. The pH drops to a low range, in one exemplary embodiment to pH 8-9, which changes the chemistry to allow de-amidation, leaving the amino acid linked glycan. Further, the method disclosed herein allows hydrolysis of the amide bonds, both peptide derived and oligosaccharide derived which result in an isolated glycan-amino acid molecule as shown in FIGS. 6 and 8. This isolation and allowance has not been performed by previously documented methods.

By "glycoprotein" is meant a protein-oligosaccharide compound where the protein and oligosaccharide portion are covalently linked. As used herein, the protein portion of the glycoprotein includes at least one covalently attached amino acid. The protein portion can be made up of naturally occurring amino acids or non-naturally occurring amino acids. By "oligosaccharide" is meant at least two monosaccharide sugars covalently linked together. Oligosaccharides in glycoproteins are generally N-linked oligosaccharides and O-linked oligosaccharides. By "O-linked oligosaccharide" is meant an oligosaccharide covalently attached to a serine, threonine or tyrosine residue of a glycoprotein. Exemplary glycoproteins include kappa casein, thyroglobulin, the secretions of mucous membranes (i.e. mucins), and fetuin.

The methods herein are preferably performed in aqueous liquid solutions. Further, the methods described herein preferably maintain the stability of the O-linked oligosaccharides such that they can be readily detected for subsequent analysis.

Therefore, methods of isolating and analyzing oligosaccharides from glycoproteins that are simple and maximize a preferred pH stability required to specifically isolate an O-linked glycan amino acid and improves upon the art have been provided.

From the above discussion and accompanying figures and claims it will be appreciated that the methods of isolating and analyzing oligosaccharides from glycoproteins offer many advantages over the prior art. It will also be appreciated by those skilled in the art that other modifications could be made without parting from the spirit and scope of the invention and fall within the scope of the claims and are intended to be covered thereby.

What is claimed:

1. A method of oligosaccharide isolation and analysis comprising the steps of:
   treating a glycoprotein sample to cleave N-linked oligosaccharides from the sample to form a first solution containing a residual protein;
   passing the first solution in an ammonium form cation exchange resin within an ion exchange cartridge by washing the cartridge with a predetermined amount of ammonium hydroxide solution to form a second solution eluted from the cation exchange resin;
   adding a predetermined amount of sodium borohydride to the second solution to form a third solution;
   letting the third solution stand capped for a predetermined amount of time;
   letting the third solution stand uncapped for a predetermined amount of time;
   evaporating the third solution to a predetermined volume to form a fourth solution;
   mixing the fourth solution with water and passing the fourth solution through a sodium form cation exchange resin within an ion exchange cartridge and collecting an eluent off the ion exchange cartridge; and
   analyzing the eluent with an analysis device.

2. The method of claim 1 wherein the first solution is kappa casein.

3. The method of claim 1 wherein the first solution is bovine submaxillary mucin.

4. The method of claim 1 wherein the ammonium hydroxide solution is 2N.

5. The method of claim 1 wherein the amount of ammonium hydroxide solution washed is 1.0 mL.

6. The method of claim 1 wherein the amount of sodium borohydride added to the second solution is 3.0 μL.

7. The method of claim 1 wherein the third solution is evaporated to 0.2 mL.

8. A method of oligosaccharide isolation and analysis comprising of:
   treating a glycoprotein sample to cleave N-linked oligosaccharides from the sample to form a first solution containing a residue protein;
   passing the first solution through an ammonium ion cation exchange resin within an ion cation exchange cartridge, adding a predetermined amount of ammonium hydroxide solution to the ammonium ion cation exchange resin, and removing a second solution from the ion cation exchange cartridge;
   evaporating the second solution;
   adding an ammonium hydroxide solution to the evaporated second solution;
   adding a sodium borohydride solution to the second solution to form a third solution;
   injecting the third solution into an elution column;
   collecting a fourth solution from the column that produced a first chromatographic peak;
   collecting a fifth solution from the column that produced a second chromatographic peak;
   pushing the fourth solution through a first ammonium form cation exchange cartridge to form a sixth solution;
   pushing the fifth solution through a second ammonium form cation exchange cartridge to form a seventh solution;
   evaporating the sixth solution to a predetermined volume;
   evaporating the seventh solution to a predetermined volume;

pushing the evaporated sixth solution through a sodium ion cation exchange resin within an ion exchange cartridge and collecting an eighth solution off the ion exchange cartridge;

pushing the evaporated seventh solution through a sodium ion cation exchange resin within an ion exchange cartridge and collecting a ninth solution off the ion exchange cartridge; and analyzing the eighth and ninth solution with an analysis device.

9. The method of claim 8 wherein the third solution injected into the column is approximately 0.01 mL.

10. The method of claim 8 wherein the sixth and seventh solutions are evaporated to 0.2 mL.

11. The method of claim 8 wherein the ammonium hydroxide solution is 2N.

12. The method of claim 8 wherein the amount of ammonium hydroxide solution added to the second solution is 1.0 mL.

13. A method of isolating and identifying an amino acid derivative comprising of:

providing a glycoprotein; and isolating and identifying an amino acid selected from a group consisting of O-tyrosine linked kappa casein di-O-sulfo tetrasaccharide derivatives and O-di-phospho serine linked bovine submaxillary mucin disaccharide derivatives from the glycoprotein.

14. A method of oligosaccharide isolation and analysis comprising the steps of:

treating a glycoprotein sample to cleave O-linked oligosaccharides from the sample to form a first solution containing a residual protein;

passing the first solution in an ammonium form cation exchange resin within an ion exchange cartridge by washing the cartridge with a predetermined amount of ammonium hydroxide solution to form a second solution eluted from the cation exchange resin;

adding a predetermined amount of sodium borohydride to the second solution to form a third solution;

letting the third solution stand capped for a predetermined amount of time;

letting the third solution stand uncapped for a predetermined amount of time;

evaporating the third solution to a predetermined volume to form a fourth solution;

mixing the fourth solution with water and passing the fourth solution through a sodium form cation exchange resin within an ion exchange cartridge and collecting an eluent off the ion exchange cartridge; and analyzing the eluent with an analysis device.

15. A method of oligosaccharide isolation and analysis comprising of:

treating a glycoprotein sample to cleave O-linked oligosaccharides from the sample to form a first solution containing a residual protein;

passing the first solution through an ammonium ion cation exchange resin within an ion cation exchange cartridge, adding a predetermined amount of ammonium hydroxide solution to the ammonium ion cation exchange resin, and removing a second solution from the ion cation exchange cartridge;

evaporating the second solution;

adding an ammonium hydroxide solution to the evaporated second solution;

adding a sodium borohydride solution to the second solution to form a third solution, injecting the third solution into an elution column;

collecting a fourth solution from the column that produced a first chromatographic peak;

collecting a fifth solution from the column that produced a second chromatographic peak;

pushing the fourth solution through a first ammonium form cation exchange cartridge to form a sixth solution;

pushing the fifth solution through a second ammonium form cation exchange cartridge to form a seventh solution;

evaporating the sixth solution to a predetermined volume;

evaporating the seventh solution to a predetermined volume;

pushing the evaporated sixth solution through a sodium ion cation exchange resin within an ion exchange cartridge and collecting an eighth solution off the ion exchange cartridge;

pushing the evaporated seventh solution through a sodium ion cation exchange resin within an ion exchange cartridge and collecting a ninth solution off the ion exchange cartridge; and analyzing the eighth and ninth solution with an analysis device.

\* \* \* \* \*